United States Patent [19]

Corman

[11] Patent Number: 5,258,001
[45] Date of Patent: Nov. 2, 1993

[54] RETRACTABLE SCALPEL WITH BLADE-ACTIVATED LOCK

[75] Inventor: John M. Corman, Houston, Tex.

[73] Assignee: Baylor College of Medicine, Houston, Tex.

[21] Appl. No.: 755,443

[22] Filed: Sep. 5, 1991

[51] Int. Cl.⁵ ............................................. A61F 2/16
[52] U.S. Cl. ..................................... 606/167; 30/162
[58] Field of Search ........................... 606/167; 30/162

[56] References Cited

U.S. PATENT DOCUMENTS

| | | | |
|---|---|---|---|
| 1,449,408 | 3/1923 | Hull | 30/162 |
| 1,960,130 | 5/1934 | Trubel | 30/162 |
| 3,906,626 | 9/1975 | Riuli | 30/162 |
| 4,089,112 | 5/1978 | Richards | 30/162 |
| 4,233,734 | 11/1980 | Bies | 30/162 |

FOREIGN PATENT DOCUMENTS 0452580  8/1936  United Kingdom ................ 30/162

*Primary Examiner*—Edgar S. Burr
*Assistant Examiner*—Anthony H. Nguyen
*Attorney, Agent, or Firm*—Bush, Moseley & Riddle

[57] ABSTRACT

In accordance with illustrative embodiments of the present invention as disclosed herein, a retractable blade knife particularly adapted for use as a surgical scalpel or the like includes a thin metal blade positioned in a cavity inside a handle and being movable between an extended position and a retracted position. In the extended position the blade is releasably locked to the handle in response to resilience of the blade caused by flexure thereof from its relaxed condition. In one embodiment the relaxed state of the blade is slight curved, and in another embodiment, such state is substantially flat. A shoulder that locks the blade in extended position is released by pressing on a pin that extends through a slot in the handle, and the pin, also is used to shift the blade longitudinally.

2 Claims, 1 Drawing Sheet

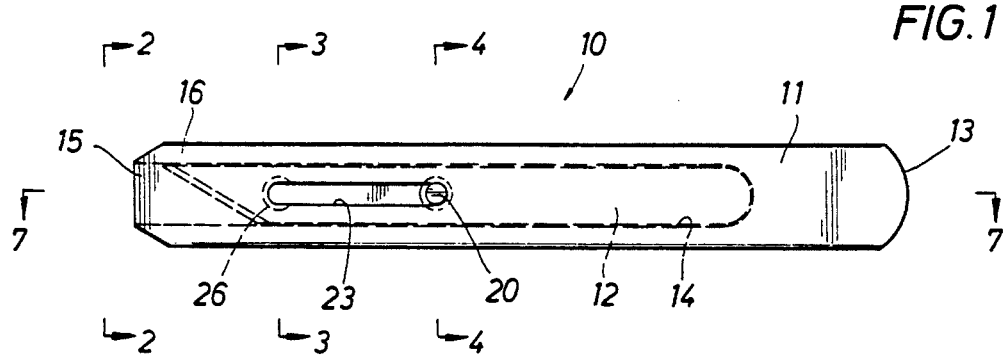
FIG. 1
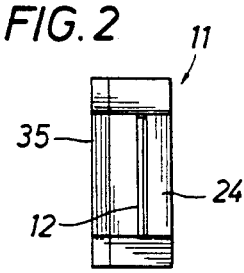
FIG. 2
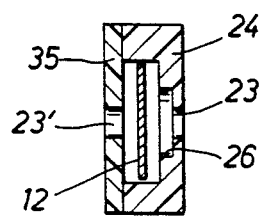
FIG. 3
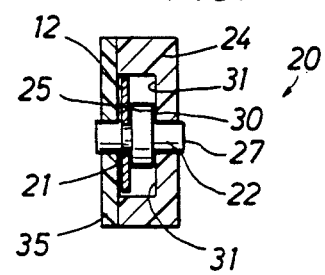
FIG. 4
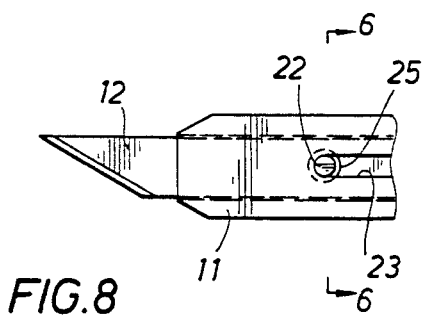
FIG. 5
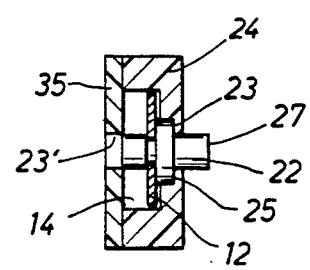
FIG. 6
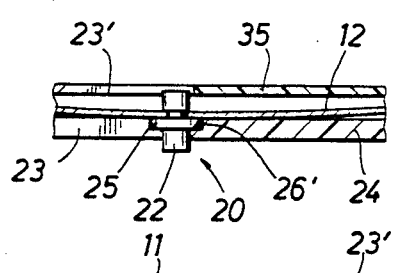
FIG. 8
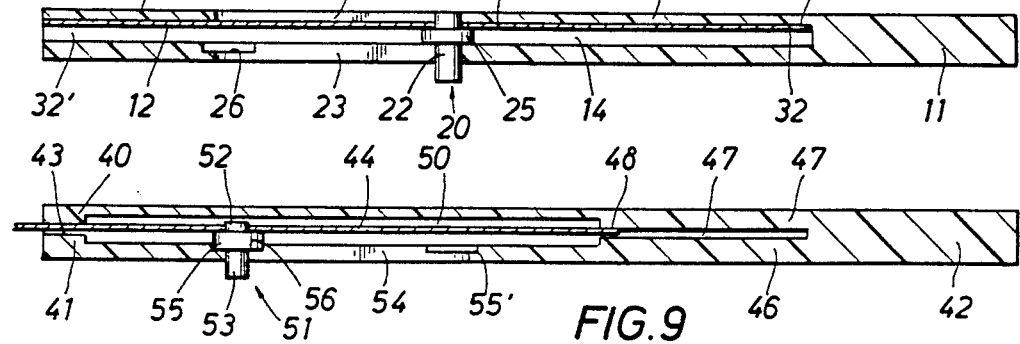
FIG. 7
FIG. 9
FIG. 10

RETRACTABLE SCALPEL WITH BLADE-ACTIVATED LOCK

FIELD OF THE INVENTION

This invention relates generally to a cutting instrument, such as a scalpel, having a retractable blade, and particularly to a new and improved cutting instrument having a blade whose resilience under flexure produces a force which activates a releasable lock in the extended position of the blade.

BACKGROUND OF THE INVENTION

Scalpels used in surgical procedures are extremely sharp and therefore somewhat dangerous to handle, particularly when being passed back and forth between the surgeon and an assistant. Unless close attention is used, which is not always possible under hectic circumstances, one or the other can sustain a cut to the hand or fingers which is not only painful but is otherwise highly undesirable. There has been a long-felt need for a scalpel that can be easily retracted before it is handed off to another person, and easily extended and locked for use in a surgical procedure. Various knives have been proposed which have retractable features. For example a Hughes U.S. Pat. No. 1,434,388 shows a knife blade having a small leaf spring on the inner end that engages notches on the edge of a channel in the handle to hold the blade in one of plurality of spaced positions. A button mounted on the spring is depressed to release the spring from the notch so that the blade can be shifted to another position. The spring is quite small and fragile, and thus apt to be broken or bent in use so that the blade is not restrained in any particular longitudinal position. The knife then becomes essentially useless because the blade can move freely in or out while cutting. A Costin U.S. Pat. No. 2,735,176 shows a spring-biased pin that extends through a hole in the blade. The pin is screwed to a button that has a boss which fits into enlarged holes at the opposed ends of a longitudinal slot in the handle. The button must be pulled outward against the bias of the spring to disengage the boss so that the blade can be extended or retracted until the boss drops back into a hole under the influence of the spring. This knife is awkward to operate because it must be held in one hand while the fingers or fingernails on the other hand are used to pull the small button out and compress the spring to disengage the boss. Particularly where the user is wearing surgical gloves that have become somewhat slippery, efforts to manipulate the button can be exasperating.

A general object of the present invention is to provide an new and improved retractable blade cutting instrument that obviates the disadvantages noted above.

SUMMARY OF THE INVENTION

This and other objects are attained in accordance with the concepts of the present invention through the provision of a new and improved cutting instrument that has particular utility as a surgical scalpel, although it could be used for other purposes. The instrument includes a handle having an elongated internal cavity that slidably receives a relatively thin metal blade which has a cutting edge on its outer end portion. In one embodiment of this invention, the blade in its relaxed state has a degree of curvature to which it tends to return when flexed to a substantially flat condition in response to lateral pressure. The blade is arranged for movement between a retracted position where the cutting edge is within the cavity, and an extended position where the front portion of the blade and the cutting edge are extended through an opening in one end of the handle. A locking and releasing pin which is fixed to a central portion of the blade projects through a longitudinal slot in a side wall of the handle and carries a shoulder adjacent the blade. The end of the slot nearest the opening is provided with an internal locking recess. The resilience of the blade produces outward pressure on the pin and the shoulder so that when the pin reaches the forward end of the slot during extension of the blade, the shoulder snaps into the recess to lock the blade extended. To release the shoulder from the recess and allow retraction of the blade, the pin is pressed inward to reduce the curvature of the blade, and then pulled rearward. During rearward movement, inward pressure need not be applied to the pin because the shoulder will ride against inner wall surfaces above and below the slot and the outward bias force of the normally curved blade produces a frictional restraint which holds the blade in the retracted position.

In another embodiment of the present invention the blade in its relaxed state is substantially flat, and the widths of the front and rear portions of the cavity are sized with respect to the width of the mid-portion thereof such that inward pressure on the pin causes the blade to assume a slight curvature which allows release of the shoulder from the locking recess. The resilience of the blade when curved forces the shoulder into the locking recess in the extended position. Structure also is disclosed for releasably locking the blade in its retracted position, if desired, and for replacing the blade. The use of the resilience of a thin metal blade to provide the lateral force which automatically activates a locking mechanism at the extended position provides a simplified and very rugged and reliable construction. The lock pin is easily released by the thumb of the same hand in which the knife is held because the shoulder is released from the recess in response to inward pressure on the pin. The thumb also can be used to slide the pin and thus the blade toward either the retracted or the extended position, and the blade automatically locks in the extended position when the shoulder reaches the locking recess at the forward end of the slot.

BRIEF DESCRIPTION OF THE DRAWINGS

The present invention has other objects, features and advantages which will become more clearly apparent in connection with the following detailed description of preferred embodiments, taken in conjunction with the appended drawings in which:

FIG. 1 is a side elevational view of a retractable blade scalpel in accordance with the present invention with the blade in its retracted position;

FIGS. 2-4 are somewhat enlarged cross-sections taken on lines 2—2, 3—3, and 4—4 of FIG. 1;

FIG. 5 is a fragmentary view similar to FIG. 1 but showing the blade extended;

FIG. 6 is an enlarged cross-section on line 6—6 of FIG. 5;

FIG. 7 is a cross-sectional view taken on line 7—7 of FIG. 1; and

FIG. 8 is a partial view similar to FIG. 7 but showing the blade also locked in retracted positions;

FIG. 9 is a cross-sectional view of another embodiment of the present invention; and FIG. 10 is a partial sectional view showing an embodiment having a replaceable blade.

DETAILED DESCRIPTION OF PREFERRED EMBODIMENTS

Referring initially to FIG. 1, a cutting instrument in the form of a scalpel indicated generally at 10 includes an elongated handle 11 having a generally rectangular cross-sectional shape. The handle 11 preferably is made of a rigid, clear plastic material such as an acrylic that is substantially transparent so that the position of the blade 12 within the handle 11 can be seen at a glance. The rear end surface 13 of the handle 11 can be somewhat rounded as shown. The blade 12, which preferably is made of a thin, surgical quality steel, is slidably received in an elongated cavity 14 in the handle 11 that opens at 15 through the outer end portion 16 thereof. For convenience, the handle 11 can have a U-shaped wall 24 that is joined to a flat side wall 35 by a suitable adhesive to form the cavity 14. Prior to installing the blade 12 within the cavity 14, the blade is bent uniformly over its length by a slight amount, so that when the blade is flattened its resilience, or tendency to return to its relaxed, slightly curved shape, produces lateral outward pressure.

When retracted, the blade 12 is held substantially flat within the cavity 14 by an enlarged diameter shoulder 25 on a lock pin 20 as shown in detail in FIG. 4. The lock pin 20 is attached to the blade 12 at a hole 21 that is located in a mid-portion of the blade, and the inner end of the pin can be bradded to provide suitable fastening. The outer portion 22 of the pin 20 extends out through an elongated slot 23 that is formed in the side wall 24 of the handle 11. The shoulder 25 is sized to fit into a generally circular internal recesses 26 (FIG. 3) formed at the outer end of the slot 23. The shoulder 25 can be an integral part of the pin 20, or could be a separate washer that is force-fitted on the pin. The scalpel 10 can be held in one hand and the outer end surface 27 of the pin 20 engaged by the thumb of the same hand to push the pin inward and release the shoulder 25 from the recess 26. The outer end portion 22 also is engaged by the thumb to slide the blade longitudinally of the handle 11.

When the blade 12 is retracted as shown in FIG. 1, its resilience forces the outer wall 30 of the shoulder 25 against the inner surfaces 31 above and below the slot 23 to frictionally hold the blade retracted. When the pin 20 is pushed forward, it will eventually reach the outer end of the slot 23, where the shoulder 25 automatically is forced to snap outward into the recess 26 by the resilience of the blade 12. The shoulder 25 remains in the recess 26 to lock the blade 12 in its extended position until it is released by inward pressure on the pin 20 as described above.

FIG. 7 shows the flexed condition of the blade 12, which normally has a slight curvature, so that it lies substantially flat within the cavity 14. The inner end 32 of the blade 12 rests against the rear side wall 33 of the cavity 14, and the outer end 32' rests against the same side wall near the opening 15. The central part 34 also lies against the side wall 33. As mentioned above, the shoulder 25 engages the wall surfaces 31 above and below the slot 23 to hold the blade 12 flat. Another slot 23' can be formed in the opposite side wall 35 of the handle to receive the head 36 by which the pin 20 is secured to the blade 12. The resilience of the blade 12, which in its relaxed state is curved slightly, forces the shoulder surfaces 30 against the wall surface 31 to frictionally hold the blade in place. Such frictional hold continues until the shoulder 25 snaps into the recess 26. To also lock the blade 12 retracted, the embodiment shown in FIG. 8 can be used. Here a locking recess 26' also is formed at the rear end of the slot 23, so that the shoulder 25 will be captured therein in the retracted position of the blade 12. However, this feature is optional, since the frictional restraint provided by engagement of the outer wall 30 of the shoulder 25 under outward pressure of the blade 12 is entirely adequate to maintain the blade in any retracted position.

FIG. 9 shows another embodiment of the present invention. In this instance the end portions 40, 41 of the front of the handle 42 are inwardly thickened to provide an opening 43 that is only slightly wider than the thickness of the blade 44. Rear portions 45, 46 of the handle 42 also are inwardly thickened and provide a gap 47 that receives the rear end portion 48 of the blade 44 as shown. A lock pin 51 is secured to a hole 52 in the central region of the blade 44 in a suitable manner such as bradding, and the height of the brad can be small enough that the slot 23' of the previous embodiment can be omitted. The outer portion 53 of the pin extends to the outside through a longitudinal slot 54, as in the previous embodiments. An internal recess 55 is formed concentric with the outer semi-circular end of the slot 54, and another recess 55' can be formed at the inner end thereof, if locking of the blade 44 in the retracted position is desired.

In this embodiment the relaxed state of the blade 44 is substantially flat as shown so that the shoulder 56 is biased outward into the recess 55 to lock the blade 44 in the extended position. Inward pressure is applied by the thumb of the user on the pin 53 to flex the blade 44 inward within the cavity 50, which releases the shoulder 56 from the recess 55 so that the blade 44 can be pulled rearward to the retracted position where the pin is at the rear of the slot 54. When the shoulder 56 arrives opposite the recess 55', it will automatically be engaged therewith by the resilience of the blade 44 as it assumes its normally flat condition.

FIG. 10 shows a modification of the cutting instrument shown in FIG. 9 which enables a used blade 44 to be removed and replaced with a new one. Although for surgical application it may be preferable to dispose of the knife, nevertheless the rear portion 60 of the handle 42 can be made as a separate part having walls 61 that telescope over companion walls 62 at the rear portion 47 of the cavity 50. The slot 54 in the side wall 46 is extended all the way to the rear edge 63 of the wall, and its height is increased at 66 to accommodate the diameter of the shoulder 56. Suitable means such as a dimple 64 on the inner surface of a wall 61 engages a depression 65 in the underlying wall to releasably retain the rear portion 60 in place. To change the blade 44, the rear portion 60 is removed and the blade is forced out the rear of the cavity portion 47 by pulling or pushing on the pin 51. A new blade 40 then is inserted into the handle 42 via the cavity portion 47, and the rear portion 60 of the handle is replaced in the position shown. A similar structure can be used to replace the blade 12 of the embodiment shown in FIGS. 1–7, as will be apparent to those skilled in the art.

OPERATION

In operation, the parts of the scalpel embodiment 10 are assembled as shown in drawings FIGS. 1–4. With the pin 20 and the shoulder 25 positioned at the rear of the slot 23, the blade 12, which in its relaxed state is slightly flexed or curved, exerts outward pressure that engages the shoulder 25 with the wall surfaces 31 as shown in FIG. 4 so that the blade 12 is frictionally held in the retracted position. To extend the front portion of the blade 12 through the opening 15, longitudinal force is applied by the thumb to the pin 20 to slide the blade 12 outward until the shoulder 25 reaches the recess 26. During longitudinal movement of the blade 12, inward pressure on the pin 20 need not be applied because the engagement of the outer walls 30 of the shoulder 25 with the inner wall surfaces 31 prevents outward flexure of the blade. The low frictional restraint to sliding of the shoulder 25 along these surfaces provides the advantage of preventing the blade 12 from going one way or the other absent manual manipulation. When the shoulder 25 reaches the recess 26, the resilience of the blade 12 forces it to snap outward into the recess and thereby lock the blade in the extended position as shown in FIG. 5. To retract the blade 12, inward pressure is applied to the outer surface 27 of the pin 20 to flex the blade 12 inward and release the shoulder 25 from the recess 26. Then the blade 12 is slid rearward to its retracted position shown in FIG. 1. When the shoulder 25 snaps into the recess 26 in the extended position, an audible click can be heard to indicate the fact of locking, and outward pin movement also can be felt by the thumb. Thus there are positive indications that the blade 12 is locked and ready for use.

The embodiment shown in FIG. 9 operates in a similar manner. Assuming the normally flat blade 44 is in the retracted position, it will have a slight curvature due to the thickness of the shoulder 56 and its engagement with the inner walls of the cavity 50 above and below the slot 54. The resilience of the blade 44 produces frictional resistance to sliding of the shoulder 56 which holds the blade retracted. In the alternative, the recess 55' can be used to positively lock the blade 44 retracted. In the former mode, the thumb is used to slide the pin 53 and the blade 44 forward, and when the shoulder 56 reaches the recess 55, it will automatically snap out in the recess to lock the blade in the extended position as shown in FIG. 9. In the latter case the thumb is used to push the pin 53 inward to flex the blade 44 and release the shoulder 56 from the recess 55', after which the pin is pushed forward and to cause the shoulder to move to, and snap into, the recess 55, The rear portion 47 of the cavity 50 has a length such that the rear end of the blade 44 does not disengage from it in the extended position. During longitudinal movement, inward pressure need not be applied to the pin 53 because the shoulder 56 prevents outward flexure of the blade 44.

It now will be recognized that new and improved retractable scalpels have been disclosed which meet the objectives and which have all the features and advantages of the present invention. Since the spring action which locks the blades 12 or 44 in the extended position is supplied by the blades themselves, the constructions are very simple, sturdy and rugged. By virtue of the fact that inward pressure of the thumb is used to release the shoulders 25, 56 from the recesses 26, 55, rather than an outward pull, the scalpels 10 be operated by one hand. The retractable nature of the present invention eliminates the major cause of "sharp" accidents during surgery which can occur when an open scalpel is handed back and forth between the surgeon and an assistant.

Although the present invention has been disclosed in the form of a surgical scalpel, the principles are applicable to other types of cutting instruments, such as those used in veterinary medicine, model building, hunting knives, wall covering, upholstery and carpet installation, to mention but a few. Additional locking recesses can be formed at spaced points along the length of the slots 23, 54 in the event that different amounts of blade extension are desirable. Since certain changes or modifications can be made in the disclosed embodiments without departing from the inventive concepts involved, it is the aim of the appended claims to cover all such changes and modifications that fall within the true spirit and scope of the present invention.

What is claimed is:

1. A cutting instrument comprising: a handle having side walls and defining an elongated cavity between said side walls, said cavity having a rectangular cross-sectional shape and opening to the outside of said handle at the forward end thereof; a resilient thin metal blade slidably mounted in said cavity, said blade being normally curved throughout its length and having a front portion with a cutting edge and being movable between a retracted position in said cavity and an extended position where said front portion projects through said opening; said blade having a thickness that is substantially less than the width of said cavity throughout the length of said cavity so that said blade can be flexed therein from its normally curved shape to a substantially flat shape; shoulder means attached to said blade and engaging internal wall surfaces of one of said side walls and holding said blade in said flat shape so that the resilience of said blade forces said shoulder means against said internal wall surfaces to frictionally hold said blade in said retracted position; means to allow shifting of said shoulder means and blade to said extended position; and means cooperable with said shoulder means in response to said forces to releasably lock said blade in said extended position.

2. A cutting instrument comprising: a handle having side walls and defining an elongated cavity between said side walls, said cavity having a rectangular cross-sectional shape; a narrow opening to the outside of said handle at the forward end of said cavity, and a narrow recess in said handle at the rear end of said cavity; a normally straight, resilient, thin metal blade having a rear portion slidably mounted in said recess and a midportion slidably mounted in said cavity, said blade having a front portion with a cutting edge and being movable between a retracted position in said handle and an extended position where said front portion projects through said narrow opening; said blade having a thickness that is substantially less than the width of said cavity so that said blade can be flexed therein from its normally straight shape to a curved shape; shoulder means attached to said blade and engaging internal wall surfaces of one of said side walls and holding said blade in said flat shape so that the resilience of said blade forces said shoulder means against said internal wall surfaces to frictionally hold said blade in said retracted position; means to allow shifting of said shoulder means and blade to said extended position; and means cooperable with said shoulder means in response to said forces to releasably lock said blade in said extended position.

* * * * *